(12) United States Patent
Hinchcliffe

(10) Patent No.: US 7,294,478 B1
(45) Date of Patent: Nov. 13, 2007

(54) MICROARRAY REACTION CARTRIDGE

(75) Inventor: John Hinchcliffe, Seattle, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 922 days.

(21) Appl. No.: 10/092,285

(22) Filed: Mar. 5, 2002

Related U.S. Application Data

(60) Provisional application No. 60/296,495, filed on Jun. 6, 2001.

(51) Int. Cl.
*G01N 33/53* (2006.01)

(52) U.S. Cl. ..................................... 435/7.9

(58) Field of Classification Search ............... 435/7.9, 435/7.91, 7.92, 4, 6, 7.1, 287.3, 287.9, 288.4, 435/288.5, 973; 436/514, 517, 518; 422/58, 422/63, 68.1
See application file for complete search history.

(56) References Cited

U.S. PATENT DOCUMENTS

| | | | | |
|---|---|---|---|---|
| 3,582,285 | A * | 6/1971 | Hamilton | 422/61 |
| 3,726,597 | A * | 4/1973 | Dvorak et al. | 356/244 |
| 4,435,508 | A * | 3/1984 | Gabridge | 435/297.5 |
| 5,417,576 | A * | 5/1995 | Hill | 435/288.3 |
| 5,474,796 | A * | 12/1995 | Brennan | 427/2.13 |
| 5,510,270 | A | 4/1996 | Fodor et al. | |
| 5,539,083 | A | 7/1996 | Cook et al. | |
| 5,543,114 | A * | 8/1996 | Dudek | 422/102 |
| 5,545,522 | A | 8/1996 | Van Gelder et al. | |
| 5,556,752 | A | 9/1996 | Lockhart et al. | |
| 5,578,832 | A | 11/1996 | Trulson et al. | |
| 5,716,785 | A | 2/1998 | Van Gelder et al. | |
| 5,770,441 | A * | 6/1998 | Lipton | 435/289.1 |
| 5,891,636 | A | 4/1999 | Van Gelder et al. | |
| 5,922,591 | A | 7/1999 | Anderson et al. | |
| 5,955,028 | A * | 9/1999 | Chow | 422/63 |
| 6,028,189 | A | 2/2000 | Blanchard | |
| 6,043,080 | A | 3/2000 | Lipshutz et al. | |
| 6,050,719 | A | 4/2000 | Winkler et al. | |
| 6,140,044 | A | 10/2000 | Besemer et al. | |
| 6,159,727 | A | 12/2000 | Bochikariov | |
| 6,203,987 | B1 | 3/2001 | Friend et al. | |
| 6,225,645 | B1 | 5/2001 | Zhang | |
| 6,238,910 | B1 | 5/2001 | Custance et al. | |
| 6,258,593 | B1 * | 7/2001 | Schembri et al. | 435/287.2 |
| 6,271,002 | B1 | 8/2001 | Linsley et al. | |
| 6,534,008 | B1 * | 3/2003 | Angros | 422/64 |
| 6,602,702 | B1 * | 8/2003 | McDevitt et al. | 435/288.7 |
| 6,803,019 | B1 * | 10/2004 | Bjornson et al. | 422/66 |

FOREIGN PATENT DOCUMENTS

| | | |
|---|---|---|
| WO | WO 98/41531 | 9/1998 |
| WO | WO 99/66024 | 12/1999 |
| WO | WO 00/24936 | 5/2000 |
| WO | WO 01/05935 | 1/2001 |

OTHER PUBLICATIONS

Baltimore, 2001, "Our genome unveiled", Nature 409:814-816.
Blanchard et al., 1996, "High-Density oligonucleotide arrays", Biosensors and Bioelectronics 11:687-690.
Bonaldo et al., 1996, "Normalization and Subtraction: Two Approaches to Facilitate Gene Discovery" Genome Research 6:791-806.
Chirgwin et al., 1979, "Isolation of biologically active ribonucleic acid from sources enriched in ribionuclease", Biochemistry 18:5294-5299.
DeRisi et al., 1996, "Use of a cDNA microarray to analyse gene expression patterns in human cancer", Nature Genetics 14:457-460.
de Wildt et al., 2000, "Antibody arrays for high throughput screening of antibody-antigen interactions", Nature Biotechnology 18:989-994.
Egholm et al., 1993, "PNA hybridizes to complementary oligonucleotides obeying the Watson-Crick hydrogen-bonding rules", Nature 365:566-568.
Fodor et al., 1991, "Light-directed, spatially addressable parallel chemical synthesis", Science 251:767-773.
Froehler et al., 1986, "Synthesis of DNA via deoxynucleoside H-phosphonate intermediates", Nucleic Acids Research 14:5399-5407.

(Continued)

*Primary Examiner*—Ann Y. Lam
(74) *Attorney, Agent, or Firm*—Jones Day

(57) ABSTRACT

An apparatus and method are provided for shipping, storing, and high-throughput processing of microarrays. An exemplary microarray cartridge according to the present invention includes a body having a cavity defined by an outer surface and two dimple features in fluid communication with the cavity. The cavity includes at least one ledge for supporting a microarray of biological probes, and a reaction chamber defined at least in part by the ledge. A plate covers the cavity and sealingly attaches to the outer surface of the body. Ports in the plate or the dimple features allow introduction of sample, reaction and wash solutions into the reaction chamber such that the solutions contacts the probes on the microarray. The disposable microarray cartridges of the present invention are used to package and store microarrays prior to use and to process microarrays in a high-throughput manner. The footprint of the cartridge is designed to be compatible with standard robotic formats or standard re-formatting approaches.

32 Claims, 9 Drawing Sheets

OTHER PUBLICATIONS

Goffeau et al. 1996, "Life with 6000 genes", Science 274:546-567.

Hughes et al., 2001, "Expression profiling using microarrays fabricated by an ink-jet oligonucleotide synthesizer", Nature Biotechnology 19:342-347.

Lockhart et al., 1996, "Expression monitoring by hybridization to high-density oligonucleotide arrays", Nature Biotechnology 14:1675-1680.

MacBeath and Schreiber, 2000, "Printing proteins as microarrays for high-throughput function determination" Science 289:1760-1763.

Maskos and Southern, 1992, "Oligonucleotide hybridizations on glass supports: a novel linker for oligonucleotide synthesis and hybridisation properties of oligonucleotides synthesised in situ", Nucleic Acids Research 20:1679-1684.

McBride et al., 1983, "An investigation of several deoxynucleoside phosphoramidites useful for synthesizing deoxyoligonucleotides", Tetrahedron Letters 24:245-248.

Nguyen et al., 1995, "Differential gene expression in the Murine Thymus Assayed by quantitative hybridization of arrayed cDNA clones", Genomics 29:207-216.

Pease et al., 1994, "Light-generated oligonucleotide arrays for rapid DNA sequence analysis", Proc. Natl. Acad. Sci. USA 91:5022-5026.

Rogers et al., 2000, "The Global Spread of Malaria in a Future, Warmer World", Science, 289:1763.

Ross et al., 2000, "Systsematic variation oin gene expression patterns in human cancer cell lines", Nature Genetics 24:227-235.

Schena et al., 1995, "Quantitative monitoring of gene expression patterns with a complementary DNA microarray", Science 270:467-470.

Schena et al., 1996, "Parallel human genome analysis; microarray-based expression of 1000 genes", Proc. Natl. Acad. Sci. USA 93:10614-10619.

Shalon et al., 1996, "A DNA microarray system for analyzing complex DNA samples using two-color fluorescent probe hybridization", Genome Research 6:639-645.

Zhu et al., 2001, "Global analysis of protein activities using proteome chips", Science 293:2101-2105.

\* cited by examiner

MICROARRAY REACTION CARTRIDGE

This application claims benefit of U.S. provisional patent application Ser. No. 60/296,495, filed Jun. 6, 2001, which is incorporated by reference herein in its entirety.

1. FIELD OF THE INVENTION

The present invention relates generally to the processing of microarrays, and particularly to a method and apparatus for storing, shipping and high-throughput processing of microarrays.

2. BACKGROUND OF THE INVENTION

Microarrays for high-throughput analysis of biological compounds are known in the biotechnology field. Microarrays generally consist of a substrate, such as a slide or chip made of glass, plastic or silicon, upon which is attached an array of biological probes representing discrete binding or reaction sites for target biological compounds. Various types of probes are known, including nucleic acids, proteins, ligands, antibodies or other cellular proteins. For example, a typical DNA microarray includes an array, or matrix, of DNA probes representing discrete binding sites for at least some of the genes or gene products (e.g., cDNAs, mRNAs, cRNAs, polypeptides, and fragments thereof) in an organism's genome.

Microarrays have various applications, depending upon the probes used and the target compounds to be analyzed. For example, DNA microarrays have been used to study gene expression profiles, such as analyzing the transcriptional state of a cell exposed to graded levels of a drug of interest. Protein microarrays, including proteome microarrays representing most or at least some encoded proteins for a particular organism, may be used to study a wide variety of biochemical activities, such as protein-protein interactions, protein-lipid interactions, identifying the substrates of protein kinases, or identifying the protein targets of small molecules (MacBeath and Schreiber, 2000, *Science* 289: 1760-1763; Zhu et al., 2001, *Science* 293:2101-2105). Similarly, a microarray having an ordered array or matrix of antibodies may be used for high-throughput screening of antibody-antigen interactions (de Wildt et al., 2000, *Nature Biotechnology* 18:989-994).

While microarrays are generally known and used in a wide variety of applications, available apparatus and systems for storing and processing microarrays have several shortcomings. For example, microarrays are typically placed in conventional microscope slide boxes or similar containers, which may not provide adequate protection during shipping and storage. Moreover, there is a potential to damage the microarray substrate or disrupt the array of biological probes when placing microarrays into, or removing them from, such a container.

During high-throughput processing of biological samples using microarrays, a common bottleneck is the selective binding or other reaction step between biological probes on a microarray and target compounds in the biological sample of interest. In the case of nucleic acid microarrays, for example, the selective binding step is often called the "hybridization" step, and is the process by which cDNA, cRNA or other nucleic acids in a sample bind selectively (i.e., hybridize) to complementary nucleic acid probe sequences (e.g., DNA or RNA) on the substrate. Preferable experimental protocols are best implemented if microarrays can be processed in pairs (sample vs. control or reference) or groups. Prior to the present invention, however, no suitable microarray processing apparatus or methods were available to handle microarray hybridization or other reactions in pairs or groups (analogous to 96-well plates, microcentrifuge tubes, or multi-well strips) for high-throughput sample processing.

In addition to their inability to process groups of samples, previously disclosed microarray processing systems have several other disadvantages. For example, many of the available hybridization devices utilize mechanical sealing mechanisms and fasteners, such as removable screws, clips, latches, screw caps and gaskets. Such devices are not desirable or practical for high-throughput processing of microarrays as they are generally closed systems, relatively complicated to use, expensive to manufacture, and/or they are not configurable with standard format footprints. Alternatively, systems employing plastic bags are relatively simple and inexpensive, however they do not provide sufficient rigidity for use with liquid dispensing robots. Other relatively simple systems utilize coverslip-type hybridization chambers placed on a microarray slide, however such systems have insufficient hybridization solution volumes and do not provide protection for microarray slides during processing or storage. Thus, there exists a need for efficient, cost-effective apparatus and methods for shipping, storing, and high-throughput processing of all types of microarrays.

Discussion or citation of a reference herein shall not be construed as an admission that such reference is prior art to the present invention.

3. SUMMARY OF THE INVENTION

An apparatus and method are provided for shipping, storing, and high-throughput processing of microarrays. In particular, the present invention is directed to a dual purpose packaging/reaction cartridge for performing high-throughput hybridization of microarrays and associated processes. An exemplary microarray cartridge according to the present invention includes a body having a reaction chamber within a central cavity. The central cavity is adapted to hold a microarray slide and includes at least one ledge or other feature that supports the microarray and defines, at least in part, the volume of a reaction chamber. The geometry of the ledge or other support also aids in minimizing sample capture behind the microarray substrate. The body optionally includes one or more dimple features in fluid communication with the cavity for adding and/or removing fluids. The dimples preferably form a passage for fluid to pass around one or more edges of the microarray, and also facilitate mixing of fluids within the chamber. A plate covers the cavity and sealingly adheres to the outer surface of the body by a heat seal or other non-removable sealing means, without the aid of screws clips, clams, latches, gaskets, or other mechanical fasteners. Optional access sites, such as ports or pierceable walls, in the plate or the dimple features facilitate introduction of sample and hybridization solutions into the reaction chamber such that the solutions contact the probes on the microarray.

The disposable microarray cartridges of the present invention are used to package and store microarrays prior to use and to process microarrays in an efficient high-throughput manner. The cartridge is configured and dimensioned to be compatible with standard robotic formats or standard re-formatting approaches. The size, shape, and construction of the chamber portion of the microarray cartridge is designed to be inexpensive to manufacture and easy to use, and to provide optimal conditions for reactions between biological probes on a microarray and molecules in a biological sample. For example, the cartridges of the present invention provide for optimal sample volumes, mixing during sample exposure, and post-reaction washing in a high-throughput mode.

A preferred embodiment of the invention includes a multi-microarray cartridge having reaction chambers for a plurality of microarrays. The multi-microarray cartridge is designed to be compatible with a high-throughput robotic system with multi-channel liquid dispensing capability for injecting sample solutions, including, for example, a biological sample in a solution with one or more reagents, into the individual microarray cartridges. Exemplary robotic systems include at least four, preferably eight or more, channels. Dimples, ports, or other features can be incorporated into the cartridge design to provide suitable tolerance clearances and zones of rigidity for pipette tips or injection needles. With appropriate fixturing, samples can be transferred from 8×12 (96 well) plates or 8-strip wells directly into the multi-microarray cartridge.

An advantage of the microarray cartridges of the present invention is that microarrays can be placed directly into the cartridge by a manufacturer for shipping or they can be used to group and store microarrays in inventory for specific projects. Cartridge and microarray are ready for use with no additional handling of microarray required, thus limiting possible damage to the microarray. By using a semi-rigid design, the cartridges of the present invention are robust enough to interface with standard robotic pipetting and, as open platforms, allow for reconfigurable reaction, washing and scanning protocols. At the same time, the semi-rigid cartridges of the present invention are designed to have relatively thin walls and a minimal number of parts, thereby optimizing cost, ease-of-use, and performance characteristics (such as fluid mixing) within the reaction chamber. The relatively thin-walled construction of the disposable cartridges also allows access to the reaction chamber by piercing or cutting through the cartridge.

4. BRIEF DESCRIPTION OF THE DRAWINGS

For a better understanding of the nature and details of the invention, reference should be made to the following detailed description taken in conjunction with the accompanying drawings, in which.

Like reference numerals refer to corresponding parts throughout the several views of the drawings.

5. DETAILED DESCRIPTION

This section presents a detailed description of the apparatus of the present invention and methods of their use. In particular, Section 5.1 describes various exemplary embodiments of the microarray cartridges of the present invention, including a single microarray cartridge, a multi-microarray cartridge, and a cartridge designed to enhance fluid motion over a microarray. Section 5.2 describes microarrays generally and their methods of preparation. Section 5.3 generally describes high-throughput methods of processing microarrays using the apparatus of the present invention.

5.1. Microarray Cartridges

Figure 1:
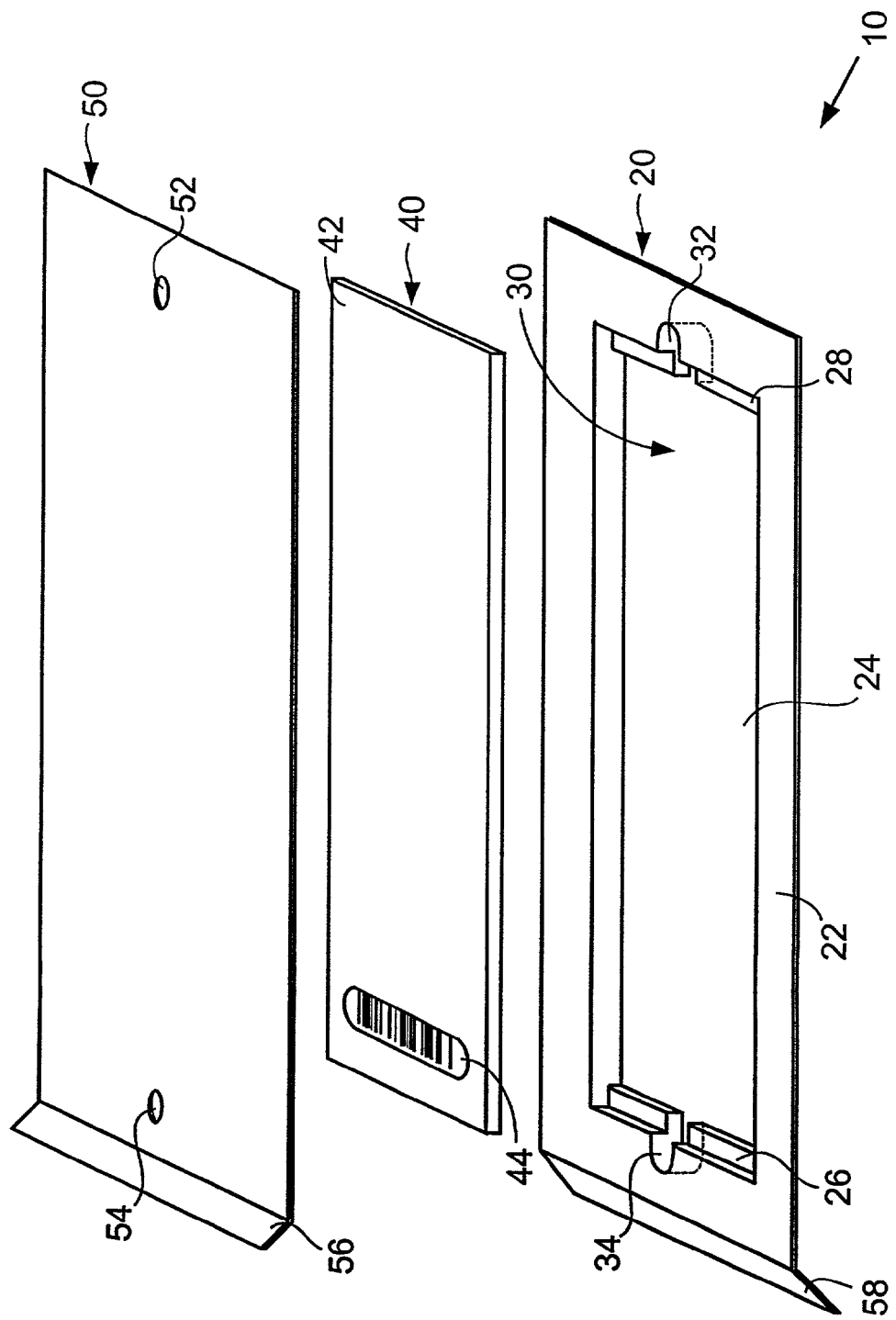
FIG. 1 is a schematic exploded perspective view of a microarray cartridge according to the present invention.

Referring to FIG. 1, an exemplary microarray cartridge 10 according to the present invention generally comprises a body 20 and a plate, or cover 50. The body 20 includes a central cavity 24 and supports, or ledges 26, 28, within the cavity for supporting a microarray 40 of nucleic acid probes. Ledges 26, 28, are configured to support microarray 40 at its edges or corners, and are preferably narrow enough to avoid contact with the probes. Ledges 26, 28 are recessed within the cavity, preferably by an amount approximately equal to or slightly greater than the thickness of microarray slide 42. While the exemplary cartridge 10 includes two ledges 26, 28 arranged to support microarray slide 40 at its ends, one skilled in the art will appreciate that other supports, such as inserts, stand-offs, spacers, bumps or other features, may be used to support slide 40 at points along its edges or corners. Alternatively, microarray 40 could be configured with support features that form a reaction chamber when microarray 40 is placed in cavity 24.

Cavity 24 includes a reaction chamber 30, that is bordered, at least in part, by ledges 26, 28 and dimples 32, 34. Microarray 40 is removably held within cavity 24 by ledges 26, 28 with the probe side of the microarray facing reaction chamber 30. The volume of reaction chamber 30 is defined, at least in part, by the geometry of ledges 26, 28 and the dimensions of cavity 24.

Body 20 optionally includes one or more dimple features 32, 34. Each dimple feature 32, 34 forms a passage for communication of fluid around slide 42, through ledges 26, 28 and into reaction chamber 30. Such dimple features may be used, for example, to introduce a sample fluid onto the probe side of microarray 40 or to wash the probes by flowing a buffer or other wash solution over microarray 40.

Cover 50 comprises a flat plate that mates with an outer portion, or mating surface, 22 of body 20. Cover 50 optionally includes access sites, such as ports 52 and 54, that correspond and co-locate with dimples, 32 and 34, respectively. Ports 52, 54 facilitate proper alignment of body 20 and cover 50 before the two are joined by a water-tight seal. Ports 52 and 54 allow introduction of sample solution, buffer, and/or other fluids into reaction chamber 30 via dimple features 32, 34. Ports 52, 54 are shown as open ports that allow introduction of fluids from robotically controlled pipettes. Alternatively, ports 52, 54 may be covered with a septum compatible with a needle for injecting solutions into ports 52, 54, where the septum re-seals after a needle is withdrawn. In a preferred embodiment of the invention, cover 50 does not include ports 52, 54; rather, samples are introduced through dimple features 32, 34, through an un-sealed edge between body 20 and cover 50, or by piercing body 20. Any such site for introducing samples is herein referred to as an "access site". After introduction of samples, the access site (e.g., an access port, an unsealed edge, or a pierced body or cover) may be sealed using adhesive, heat sealing, or the like. Cover 50 is preferably transparent, allowing bar code 44 to be scanned while microarray slide 40 is sealed in cartridge 10.

Body 20 and cover 50 are preferably sealingly adhered by non-removable adhering means, preferably a heat seal or adhesive, about the mating surface 22 of the body. As used herein, the term "non-removable adhering means" includes, but is not limited to, heat seals, adhesives, ultrasonic bonding, pressure stamping, and combinations thereof. Body 20 and cover 50 are joined together by any of such non-removable adhering means to create an adhering seal about mating surface 22 without the aid of screws, clips, clamps, latches, removable gaskets, or other mechanical fasteners or complex sealing mechanisms. Such mechanical fasteners and/or sealing mechanisms are not desirable for use with inexpensive, disposable, high-throughput systems such as the microarray cartridges of the present invention.

Components of cartridges of the present invention can be constructed from a variety of materials that are compatible with biological sample solutions. Suitable materials include, but are not limited to, polypropylenes, polycarbonates, polyethylenes, polystyrenes, polyvinylchlorides, polyacrylics, polyesters, ABS, acetal, polyether ether keytones (PEEK), polyamides, fluoro polymers, polyethylene terephthalate (PET), polyethylene terephthalate glycol (PETG), styrene acrylonitriles, and co-polymers of the above. Methods for manufacturing the cartridges include thermoforming (e.g., pressure forming or vacuum forming), injection molding, stamping, and machining, among others.

In a preferred embodiment of the present invention, cartridge 10 is a relatively thin, semi-rigid, thermoformed structure. The cartridge is preferably thermoformed from a single sheet of polymer material, such as polypropylene, a polyethylene or a polyvinylchloride. Using known thermoforming process, cartridge 10 can be made to have wall thicknesses between 0.003 and 0.065 inches, preferably between 0.005 and 0.025 inches, and most preferably between 0.010 and 0.015 inches. The resulting cartridge is rigid enough to withstand microarray packaging, handling, and sample processing by robotic instruments without damaging microarray 40. At the same time, the relatively thin-walled construction has several advantages. For example, the materials are low cost, easy to form, and provide crisp and reliable definition of features and dimensions such as reaction chamber 30 volume, microarray supports 26, 28, dimple features 32, 34 and flange features 56, 58.

The relatively thin nature of the walls of cartridge 10 may also help optimize mixing and flow characteristics within the reaction chamber 30 during hybridization or other reactions. Still another benefit of the semi-rigid and relatively thin walls of the cartridge of the present invention is that they may be easily punctured by a needle or other sharp object to allow introduction of the sample solution, or for washing or rinsing of the microarray inside the chamber. In such applications, dimple features 32, 34 provide additional zones of rigidity whereby a needle or similar device can pierce the wall of body 20 or cover 50 without collapsing any part of cartridge 10 against the microarray 40. The thin-walled, semi-rigid construction of the cartridges according to the present invention also allows easy formation of an adhering seal, such as a heat seal or compression seal, between mating surface 22 of body 20 and cover 50 without the aid of gaskets, screws, clips, clamps, latches, or other mechanical fasteners. Still another advantage of the relatively thin, semi-flexible walls of the cartridges of the present invention is that they deflect to allow entry of a pipette or other delivery device between an unsealed edge of cartridge, for example in embodiments having an opening between body 20 and cover 50 at flanges 56, 58.

In another embodiment, cartridge 10 of the present invention is formed by injection molding to produce wall thicknesses of 0.016 to 0.100 inches. Injection molding is generally known in the art. A preferred wall thickness range for an injection molded cartridge is between 0.032 and 0.075 inches, more preferably between 0.040 and 0.060 inches. In such embodiments, potential access sites for adding or removing fluids to chamber 30 include open ports (e.g., ports 52, 54) on cover 50 or body 20, an unsealed end of cartridge 10 (e.g. between flange features 56, 58) or through a relatively thin puncture site, for example a puncture site having a thickness of less than about 0.010 inch, preferably about 0.003 inch (not shown). Similarly, in injection molded (or machined) embodiments employing heat seals to adhere body 20 and cover 50, cartridge material thicknesses in the heat sealed area are preferably between 0.005 and 0.040 inches.

Figure 2:
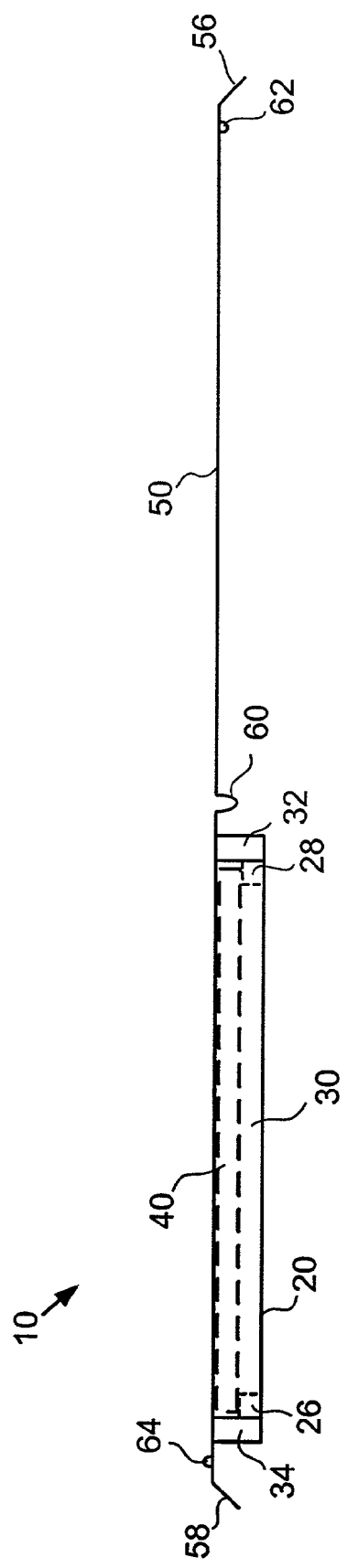
FIG. 2 is a side view of an alternative embodiment of the microarray cartridge of FIG. 1.

Referring to FIG. 2, cover 50 is optionally attached to body 20, for example by a hinge feature 60. In the exemplary embodiment shown, hinge feature 60 attaches cover 50 to body 20 along one end, and allows cover 50 to fold into place over cavity 24 of body 20. One or more optional snap features 62, 64 may be used to align cover 50 and keep it closed over body 20 prior to heat sealing. Storing microarrays 40 in cartridge with cover 50 closed helps to protect microarrays 40 and keep them free of dust and debris.

Figure 3:
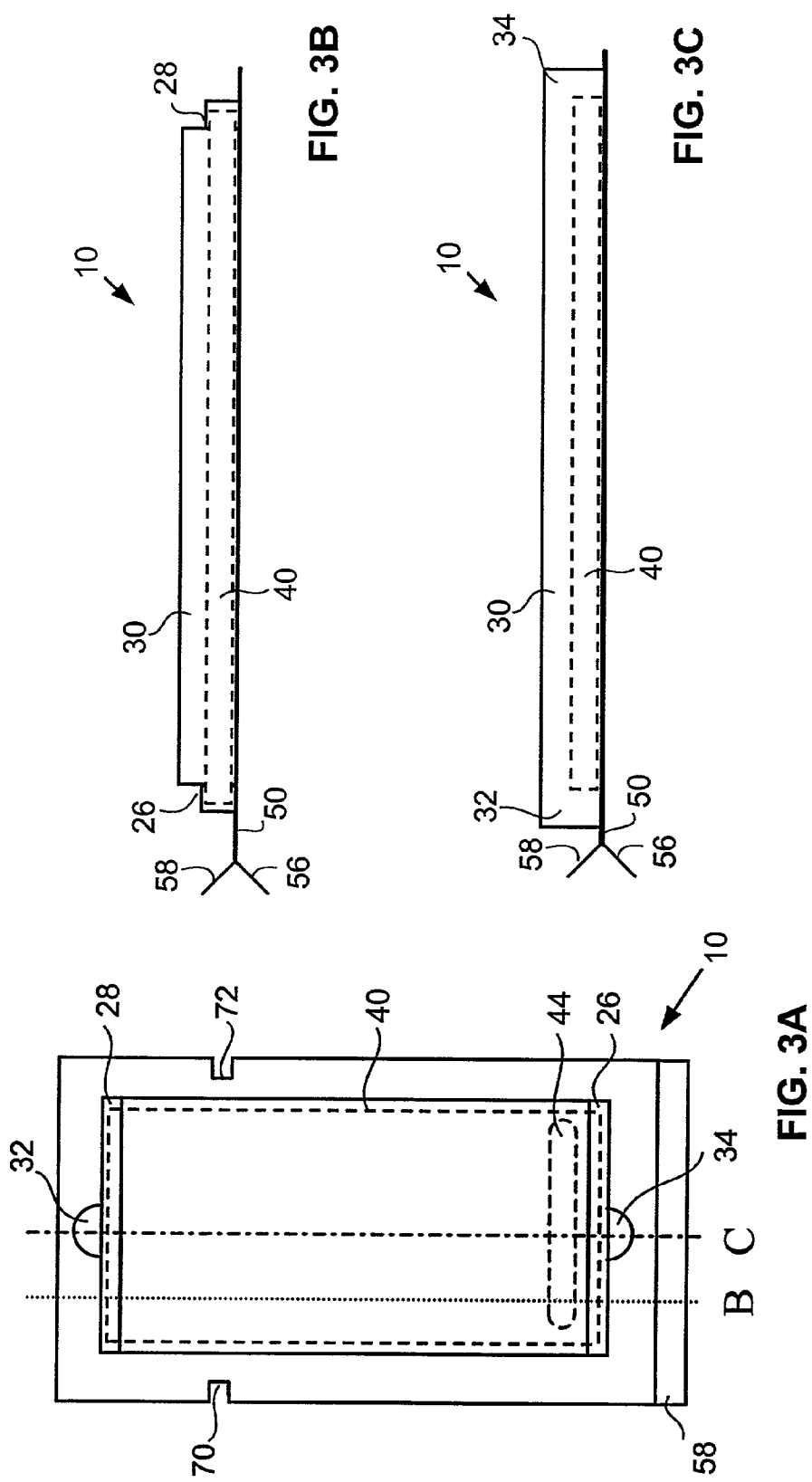
FIG. 3A is a schematic top view of a microarray cartridge according to the present invention.
FIG. 3B is a schematic cross-sectional view of the microarray cartridge of FIG. 3A, taken through line B.
FIG. 3C is a schematic cross-sectional view of the microarray cartridge of FIG. 3A, taken through line C.

Snap features 62, 64 are preferably located along an edge or corner opposite hinge feature 60; however, the type, number and location of snap features 62, 64 may vary. The mating ends of body 20 and cover 50 each optionally include a flange 56, 58, respectively, that form a fluted opening when cover 50 is closed (e.g. see FIG. 3B). The fluted opening facilitates entry of a pipette or other device into one end of cartridge 10 for introducing sample into reaction chamber 30 before sealing the end of the cartridge. A one-piece cartridge such as that shown in FIG. 2 helps to further optimize cost and ease of use by minimizing the number and complexity of components.

Referring to FIGS. 3A and 3B, ledges 26, 28 serve to catch the edges of microarray slide 40 where no probe sequences are synthesized such that the probes do not come in contact with the cartridge walls and, second, to immobilize the slide during reactions between the biological sample solution and the microarray probes. When the cartridge is oriented as shown in FIGS. 3A-C, reaction chamber 30 is where sample solution containing the processed sample (e.g., cDNA, cRNA, proteins, etc.) comes in contact with the microarray probe sequences. The volume capacity of the reaction chamber 30 can be optimized for a particular application and/or a given set of conditions. For example, a preferred embodiment of the present invention includes a chamber 30 volume capacity of 1 to 3 mL for nucleic acid hybridization uses. In various embodiments, the volume capacity of chamber 30 is greater than 500 µL, preferably greater than 1 mL.

One skilled in the art will appreciate that the volume capacity of chamber 30 of cartridge 10 is distinct from commercially available hybridization or reaction chambers, which are designed for small volumes (generally about 40 µL to 400 µL). Indeed, most of the commercial chambers are more accurately described as humidity control devices as they are really designed to prevent excessive evaporation of the small volume of biological sample solution that is pipetted under a microscope coverslip which covers the microarray probe area. In such systems, the sample solution is held in contact with the microarray throughout the hybridization or other reaction step by capillary action.

Comparing the schematic cross-sectional view of cartridge 10 in FIG. 3C with that in FIG. 3B, one can see that dimple features 32, 34 provide passages that allow introduction of fluid into chamber and/or flow of fluid over the surface of microarray 40 probes. For example, pressurized fluid flow in through one dimple feature or port and out through another may be used to optimize agitation conditions during sample exposure (i.e., the reaction step) or washing following the reaction step. As stated above, a fluid may be introduced, for example, through the fluted opening formed by flange features 56, 58 or by piercing a dimple feature or through one or more ports (not shown) in dimple features 32, 34 or in cover 50. After piercing dimple feature 32, 34 to introduce and/or withdraw fluids, for example by a robotically controlled needle device, the resulting hole may be sealed using an adhesive, a gasket, a plug, or the like. As noted above, dimple features 32, 34, as well as ports 52, 54 of FIG. 1, are optional. Sample and washing solutions may be introduced and/or withdrawn, for example, by piercing another part of body 20 or cover 50 or by passing through an opening in the seal between body 20 and cover 50.

Referring again to FIG. 3A, cartridge 10 optionally includes notches 70, 72 or other features that assist in robotic handling of the cartridge and/or in keeping the cartridge in a cartridge holder during processing or storage. Such notches 70, 72 or other features may be configured to mate with corresponding features in a cartridge holder to assure proper alignment and prevent movement of the cartridge during sample loading or other processing steps.

Figure 4:
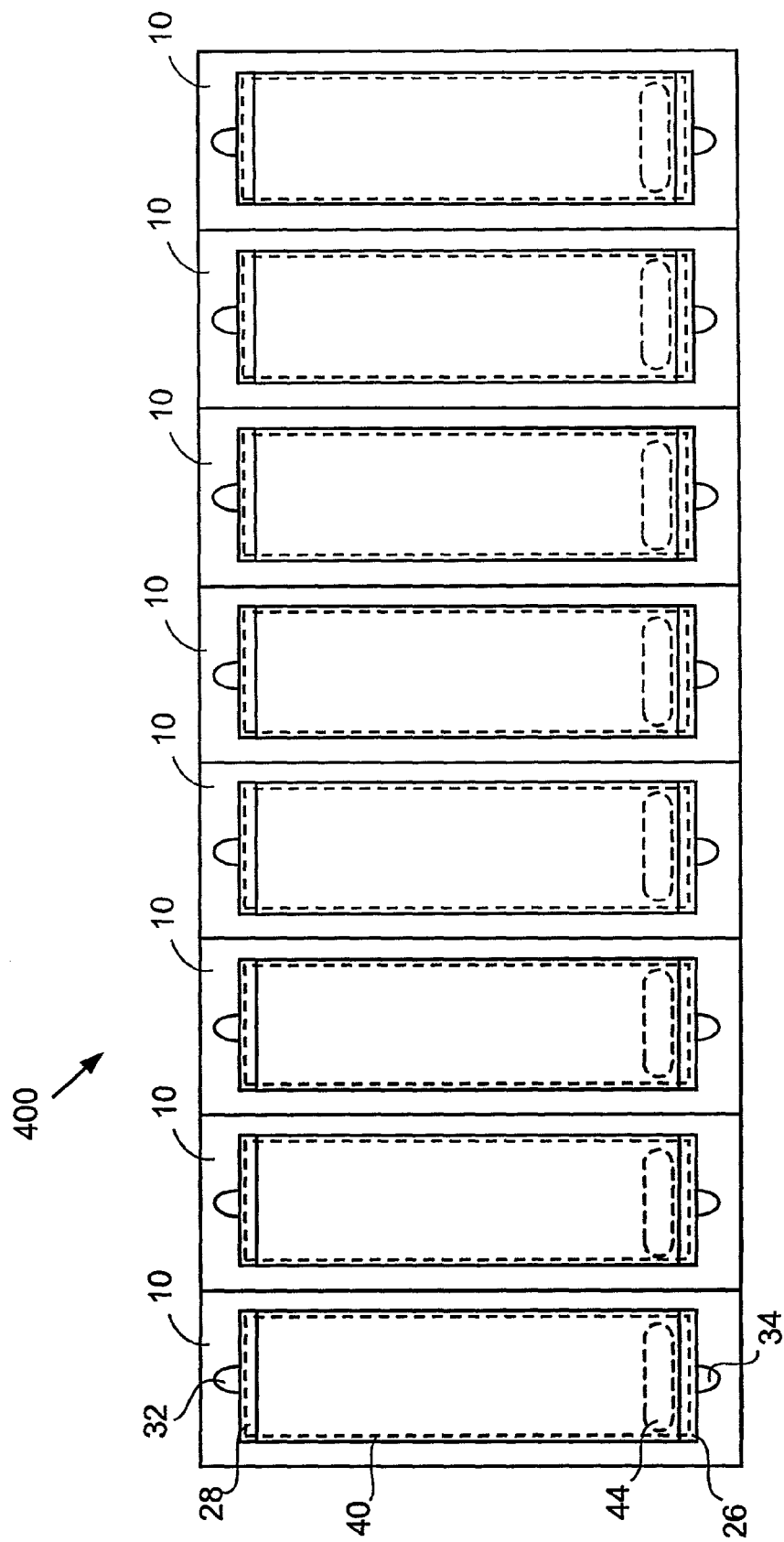
FIG. 4 is a schematic top view of a multi-microarray cartridge according to the present invention.

As shown in FIG. 4, a preferred embodiment of the invention is a multi-microarray cartridge 400 compatible with high-throughput robotic processing. Cartridge 400 is essentially comprised of a plurality, e.g., two, four, eight or more, microarray cartridges 10, each having a cavity 24 including ledges 26, 28 for holding microarray 40 and reaction chamber 30 accessible via dimple features 32, 34, as described above. The eight cartridges 10 of exemplary multi-microarray cartridge 400 may be serially attached as shown in FIG. 4 or may be formed from a single piece of material by thermoforming, injection molding, stamping, machining or another suitable processes. Cartridge 400 is designed to be compatible with a Multiprobe II HT robot (Packard Instrument Company, Downer's Grove, Ill.) with 8-channel liquid dispensing capability for injecting sample and reagent solutions into the individual microarray cartridges 10. Alternative equipment that could be used for sample injection includes the Tecan Genesis Workstation (Tecan US Inc, Durham, N.C.) or the Biomek FX automatic workstation (Beckman Coulter, Fullerton, Calif.). Other suitable robotic equipment manufacturers exist. Dimples 32, 34 and/or ports 52, 54 can be incorporated into the cartridge design to provide suitable tolerance clearances for pipette tips or injection needles. The location of dimples 32, 34 and ports 53, 54 may be varied to other positions on the cartridge depending on the type of robotic device in use. With appropriate fixturing, samples can be transferred from 8×12 (96 well) plates or 8-strip wells directly into the multi-microarray cartridge.

Aside from the advantage of using robots for high throughput injection of solutions, the multi-microarray cartridge 400 of FIG. 4 provides assurance that biological samples from an 8×12 plate are more likely to react with the correct microarray. Automation of the biological sample handling process helps to minimize errors induced by human handling of individual biological samples. In addition, cartridge 400 is preferably transparent such that bar code labels 44 on each microarray 40 can be scanned through the cartridge, thereby providing another level of insurance for proper matching of a biological sample with the appropriate microarray.

While multi-microarray cartridge 400 of FIG. 4 is shown having eight microarray cartridges 10 attached in a serial fashion, one skilled in the art will appreciate other multi-microarray cartridge embodiments may be configured for packaging and processing of any number of microarrays arranged in a variety of other formats. Another alternative is that cartridges 10 could be shipped individually and then ganged together in any fashion with heat or adhesives using a template. The template design would vary depending on the design of the high-throughput microarray facility and other considerations.

Figure 5:
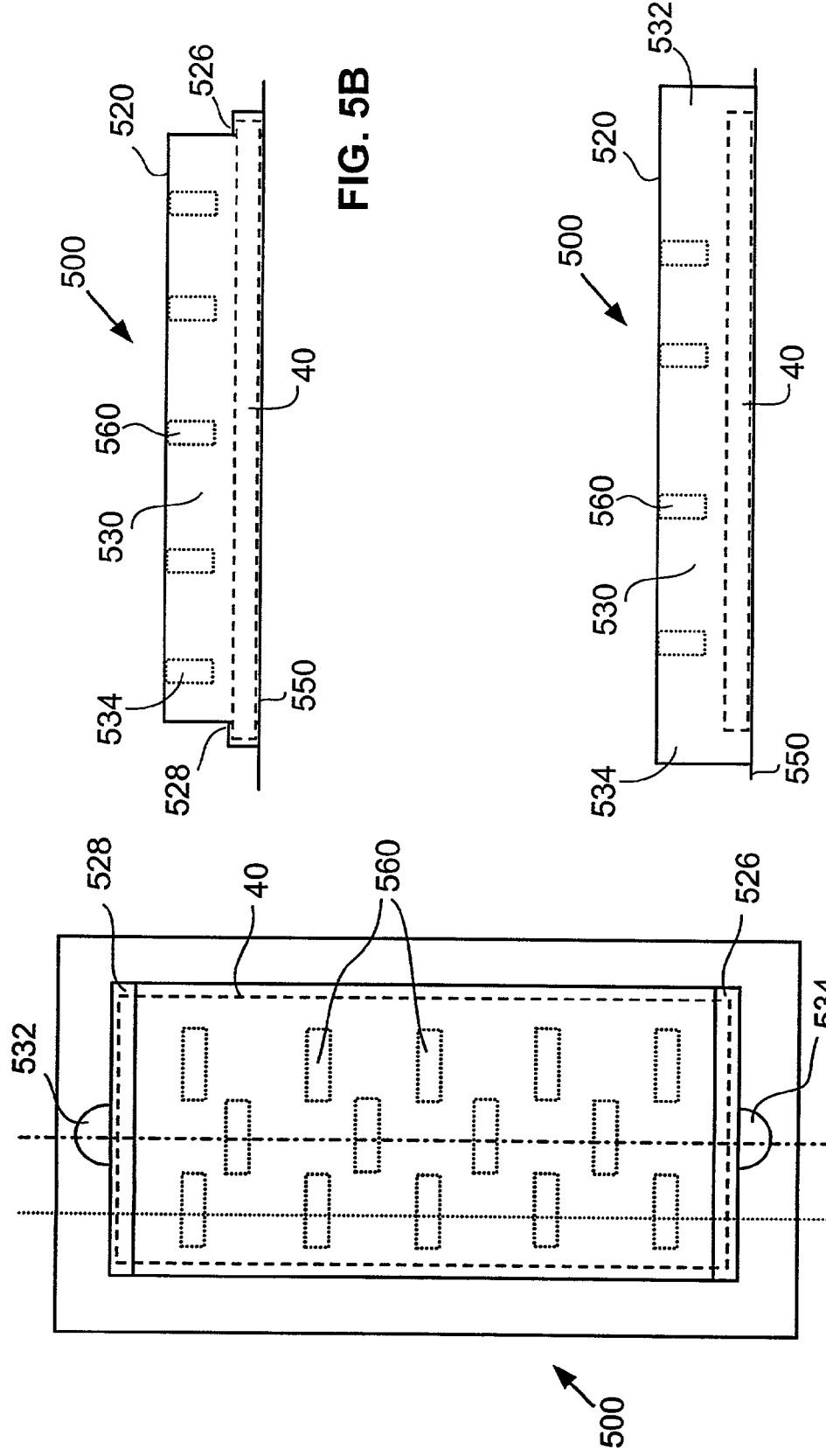
FIG. 5A is a top view of an alternative embodiment of the microarray cartridge of the present invention, having features to enhance fluid mixing.
FIG. 5B is a cross-sectional view of the microarray cartridge of FIG. 5A, taken through line B.
FIG. 5C is a cross-sectional view of the microarray cartridge of FIG. 5A, taken through line C.

Referring to FIGS. 5A-5C, another embodiment of the present invention is a microarray cartridge 500 similar to cartridge 10 of FIGS. 1-4 and constructed of similar materials. Like cartridge 10, cartridge 500 includes a body 520 with ledges 526, 528 or other supports for supporting microarray 40 and forming reaction chamber 530. Cover 550 attaches to body and seals the microarray 40 within body 520. One or more optional dimple features 532, 534 provide access to reaction chamber 530 for adding or withdrawing fluids. Alternatively, chamber 530 may be accessed by piercing body 520 or cover 550 using a needle or other instrument. Unlike cartridge 10 of FIGS. 1-4, cartridge 500 additionally includes a plurality of obstacles 560 within reaction chamber 530 to enhance fluid flow and mixing within the chamber. Obstacles 560 or similar features are designed in such a way as to not touch or damage the surface of microarray 40. Obstacles 560 may be attached to body 520 or molded or formed into body 520 of cartridge 500 by thermoforming, injection molding, or other suitable process. Optionally, obstacles 560 are one or more inserts placed in chamber 530 of cartridge 500. By way of non-limiting example, obstacles 560 serve to break up trapped air bubbles in chamber 530 and cause reagent to follow different streaming paths during the course of rocking or rotation in the oven (see section 5.3 below for a more detailed description of methods of use). One skilled in the art will appreciate that the pattern of obstacles 560 shown in FIG. 5 is exemplary, and other patterns may be used to optimize mixing and/or flow, depending in part upon the type of mixing device used (e.g., rotating wheel or rocker platform) and/or the device settings.

5.2. Microarrays Generally

While one skilled in the art will appreciate that various types of microarrays may be used in the cartridges of the present invention, including but not limited to nucleic acid microarrays, proteome microarrays (Zhu et al., 2001, *Science* 293:2101-2105), other protein microarrays (MacBeath and Schreiber, 2000, *Science* 289:1760-1763) and antibody microar-rays (de Wildt et al., 2000, *Nature Biotechnology* 18:989-994), the following description of the general characteristics and preparation of microarrays utilizes nucleic acid microarrays as a primary example. For a more detailed description of nucleic acid microarrays, see U.S. Pat. No. 6,203,987 and International Patent Publications WO 99/66024, published Dec. 23, 1999 and WO 01/05935, published Jan. 25, 2001.

A nucleic acid microarray typically comprises a surface with an ordered array of reaction (e.g., hybridization) sites for products of many of the genes in the genome of a cell or organism, preferably most or almost all of the genes. The surface is typically a solid support such as slide 42 of microarray 40, but may be any non-porous or porous substrate including, but not limited to, a glass or plastic surface or a nitrocellulose or nylon membrane or filter.

Microarrays can be made in a number of ways, of which several are described below. However produced, microarrays share certain characteristics: The arrays are reproducible, allowing multiple copies of a given array to be produced and easily compared with each other. Preferably, a given reaction site or unique set of reaction sites (i.e., probes) in the microarray will specifically bind or otherwise react to the presence or condition of a specific target compound in a biological sample. In the case of nucleic acid microarrays, for example, each probe in the array will preferably hybridize with the product of a single gene in a cell, for example a specific mRNA or a specific cDNA derived therefrom. However, in general other, related or similar sequences will cross hybridize to a given binding site. Although there may be more than one physical binding site per specific target compound or gene product, for the sake of clarity the discussion below will assume that there is a single, completely complementary binding site.

Nucleic acid microarrays typically include one or more test probes, each of which has a polynucleotide sequence that is complementary to a subsequence of RNA or DNA to be detected. Each probe preferably has a different nucleic acid sequence. The position of each probe on the solid surface is preferably known. In one embodiment, the microarray is a high density array, preferably having a density greater than about 60 different probes per 1 $cm^2$. In one embodiment, the microarray is an array (i.e., a matrix) in which each position represents a discrete binding site for a product encoded by a gene (i.e., an MRNA or a CDNA derived therefrom), and in which binding sites are present for products of most or almost all of the genes in the organism's genome. For example, the binding site can be a DNA or DNA analogue to which a particular RNA can specifically hybridize. The DNA or DNA analogue can be, e.g., a synthetic oligomer, a full-length cDNA, a less-than full length cDNA, or a gene fragment.

Although in a preferred embodiment the nucleic acid microarray contains binding sites for products of all or almost all genes in the target organism's genome, such comprehensiveness is not necessarily required. Usually the microarray will have binding sites corresponding to at least about 50% of the genes in the genome, often to about 75%, more often to at least about 85%, even more often to about 90%, and still more often to at least about 99%. Preferably, the microarray has binding sites for genes relevant to the action of a drug of interest or in a biological pathway of interest. A "gene" is identified as an open reading frame ("ORF") which encodes a sequence of amino acids (e.g. 50, 75, 99 amino acids or more) from which a messenger RNA is transcribed in the organism or in some cell in a multicellular organism. The number of genes in a genome can be estimated from the number of different mRNAs expressed by the organism, or by extrapolation from a well characterized portion of the genome. When the genome of the organism of interest has been sequenced, the number of ORF's can be determined and MRNA coding regions identified by analysis of the DNA sequence. For example, the genome of *Saccharomyces cerevisiae* has been completely sequenced, and is reported to have approximately 6275 ORFs longer than 99 amino acids. Analysis of the ORFs indicates that there are 5885 ORFs that are likely to encode protein products (Goffeau et al., 1996, *Science* 274:546-567). In contrast, the human genome is estimated to contain approximately 30,000 to 40,000 genes (see *Nature* 409:814-816, 2001).

5.2.1. Preparing Probes for Microarrays

As noted above, the "probe" in a nucleic acid microarray to which a particular polynucleotide molecule specifically hybridizes according to the invention is usually a complementary polynucleotide sequence. In one embodiment, the probes of the microarray are DNA or DNA "mimics" (e.g., derivatives and analogues) corresponding to at least a portion of each gene in an organism's genome. In another embodiment, the probes of the microarray are complementary RNA or RNA mimics.

DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtained, e.g., by polymerase chain reaction ("PCR") amplicafication of gene segments from genomic DNA, cDNA (e.g., by RT-PCR), or clones sequences. PCR primers are preferably chosen based on known sequences of the genes or cDNA that result in amplification of unique fragments (i.e., fragments that do not share more than 10 bases of contiguous identical sequence with any other fragment on the microarray). Computer programs that are well known in the art are useful in the design of primer with the required specificity and optimal amplification properties, such as Oligo version 5.0 (National Biosciences). Typically, each probe of the microarray will be between about 20 bases and about 12,000 bases, and usually between about 300 bases and about 2,000 bases in length, and still more usually between about 300 bases and about 800 bases in length. PCR methods are well known in the art, and are described, for example, in Inis et al., eds., 1990, *PCR Protocols: A Guide to Methods and Applications*, Academic Press Inc., San Diego, Calif. It will be apparent to one skilled in the art that controlled robotic systems are useful for isolating, purifying and amplifying nucleic acids.

An alternative means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 500 bases in length, more typically between about 20 and about 60 bases. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Eghohm et al., 1993, *Nature* 363:566-568; U.S. Pat. No. 5,539,083).

In alternative embodiments, the reaction sites (i.e., the probes) are made from plasmid or phage clones of genes, cDNAs (e.g., expressed sequence tags), or inserts therefrom (Nguyen et al., 1995, *Genomics* 29:207-209).

In other alternative embodiments, the probes are proteins attached covalently onto chemically derivatized glass or plastic slides, wherein the proteins retain their folded conformations and thus their ability to react with other proteins, substrates of protein kinases and/or other small molecules, as described in MacBeath and Schreiber, 2000, *Science* 289:1760-1763. Similarly, proteome microarrays (also called "proteome chips") having a large number of encoded proteins for a particular organism arrayed on the surface of a slide or chip may be used, for example, to screen for protein-drug interactions or to detect posttranslational modifications, as described in Zhu et al, 2001, *Science* 293:2101-2105. In still other alternative embodiments, the probes are antibodies attached in an array to a slide or chip, where each antibody probe selectively reacts with a particular antibody as described in de Wildt et al., 2000, *Nature Biotechnology* 18:989-994.

5.2.2. Attaching Probes to the Solid Surface

The probes are attached to a solid support or surface, which may be made, e.g., from glass, plastic (e.g., polypropylene, nylon), polyacrylamide, nitrocellulose, or other materials. A preferred method for attaching the probes to a surface is by printing on glass plates, as is described generally by Schena et al, 1995, *Science* 270:467-470. This method is especially useful for preparing microarrays of cDNA (See also, DeRisi et al., 1996, *Nature Genetics* 14:457-460; Shalon et aL, 1996, *Genome Res.* 6:689-645; and Schena et al., 1995, *Proc. Natl. Acad. Sci. U.S.A.* 93:10539-11286). Blanchard discloses the use of an ink jet printer for oligonucleotide synthesis using propylene carbonate as solvent (U.S. Pat. No. 6,028,189 and WO 98/41531, published Sep. 24, 1998).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251: 767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510, 270) or other methods for rapid synthesis and deposition of defined oligonucleotides (Blanchard et al., *Biosensors & Bioelectronics* 11:687-690). When these methods are used, oligonucleotides (e.g., 20-mers) of known sequence are synthesized directly on a surface such as a derivatized glass slides. Usually, the array produced is redundant, with several oligonucleotide molecules per RNA. Oligonucleotide probes can be chosen to detect alternatively spliced mRNAs. In a specific embodiment, the oligonucleotides probes include 40-70 nucleotides, preferably 50-60 nucleotides (Hughes et al., *Nat. Biotech.* 19:342-347, 2001).

In the case of protein microarrays, for example, protein probes may be printed on glass or plastic slides using a high-precision contact-printing robot (e.g., GMS 417 Arrayer, Affymetrix, Santa Clara, Calif.) to deliver nanoliter volumes of hydrated protein samples to the slides. Depending upon the proteins used, it may be preferable to utilize treated slides such as aldehyde slides or BSA-N-hydroxysuccinimide slides (MacBeath and Schreiber, 2000, *Science* 289:1760-1763).

Other methods for making microarrays, e.g., by masking (Maskos and Southern, 1992, *Nuc. Acids. Res.* 20:1679-1684), may also be used. In principle, any type of array, for example, dot blots on a nylon hybridization membrane (see Sambrook et al., supra) could be used. However, as will be recognized by those skilled in the art, very small arrays will frequently be preferred because hybridization volumes will be smaller.

5.2.3. Target Polynucleotide Molecules

The polynucleotide molecules which may be analyzed by nucleic acid microarrays within the cartridges of the present invention (the "target polynucleotide molecules") may be from any source, but are expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly(A)+messenger RNA (MRNA) or fractions thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. Nos. 5,545,522, 5,891,636, or 5,716,785). Methods for preparing total and poly(A)+RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al, 1979, *Biochemistry* 18:5294-5299). In another embodiment, total RNA is extracted using a silica gel-based column, commercially available examples of which include RNeasy (Qiagen, Valencia, Calif.) and StrataPrep (Stratagene, La Jolla, Calif.). In an alternative embodiment, which is preferred for *S. cerevisiae*, RNA is extracted from cells using phenol and chloroform, as described in Ausubel et al. (Ausubel et aL, eds., 1989, *Current Protocols in Molecular Biology*, Vol III, Green Publishing Associates, Inc., John Wiley & Sons, Inc., New York, at pp. 13.12.1-13.12.5). Poly(A)$^+$ RNA can be selected, e.g., by selection with oligo-dT cellulose or, alternatively, by oligo-dT primed reverse transcription of total cellular RNA. In one embodiment, RNA can be fragmented by methods known in the art, e.g. by incubation with $ZnCl_2$, to generate fragments of RNA. In another embodiment, the polynucleotide molecules analyzed by the invention comprise cDNA, or PCR products of amplified RNA or cDNA.

In a preferred embodiment, total RNA, MRNA, or nucleic acids derived therefrom, from a wide number of diverse types of cells of the genome of interest are contacted with the genomic microarrays of the invention, so that all, or substantially all exons in a given cell's genome are detected, since different cell types express different levels of RNAs. Cells of interest include, but are by no means limited to, wild-type cells, mutant cells, drug-exposed wild-type cells, drug-exposed mutant cells, primary cells, cell lines, cells of different tissues or developmental stages, modified cells, diseased cells and cancer cells. Target polynucleotide molecules that are poorly expressed in particular cells may be enriched using normalization techniques (Bonaldoi et al., 1996, *Genome Res.* 6:791-806).

As described above, the target polynucleotides are detectably labeled at one or more nucleotides. Any method known in the art may be used to detectably label the target polynucleotides. Preferably, this labeling incorporates the label approximately uniformly along the length of the RNA, and more preferably, the labeling is carried out at a controlled, reproducible efficiency. One embodiment for this labeling uses oligo-dT primed reverse transcription to incorporate the label; however, conventional methods of this method are biased toward generating 3' end fragments. Thus, in a preferred embodiment, random primers (e.g., 9-mers) are used in reverse transcription to uniformly incorporate labeled nucleotides over the full length of the target polynucleotides. Alternatively, random primers may be used in conjunction with PCR methods or T7 promoter-based in vitro transcription methods in order to amplify the target polynucleotides.

In a preferred embodiment, the detectable label is a luminescent label. For example, fluorescent labels, bio-luminescent labels, chemi-luminescent labels, and colorimetric labels may be used in the present invention. In a highly preferred embodiment, the label is a fluorescent label, such as a fluorescein, a phosphor, a rhodamine, or a polymethine dye derivative. Examples of commercially available fluorescent labels include, for example, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.). In another embodiment, the detectable label is a radiolabeled nucleotide.

In a further preferred embodiment, target polynucleotide molecules from two or more different sources are distinguishably labeled, such as with different color labels. In a highly preferred embodiment, these different sources are chosen so as to maximize the differential expression of genes of interest. The skilled artisan will appreciate that differentially expressed exons are easier to detect in this manner. For example, target polynucleotide molecules can be isolated from diverse tissues or growth conditions and distinguishably labeled with different color labels for each source of molecules. In some embodiments of the invention, at least 2, 5, 10, 20, or 100 dyes of different colors can be used for labeling.

In one embodiment, such diverse conditions can be determined using a large collection of known genes and examining the correlation of their expression in pairwise combinations of experimental conditions. For example, the correlation data may be based on expression data from at least 2, 5, 10, 100, 500, 2,000, 10,000, or 50,000 different conditions. Conditions of interest include, but are by no means limited to, wild-type cells, mutant cells, drug-exposed wild-type cells, drug-exposed mutant cells, primary cells, cell lines, cells of different tissues or developmental stages, modified cells, diseased cells and cancer cells. The correlation data are used to assemble clusters of related conditions (Ross et al., *Nature Genet.* 24, 227-35, 2000; Friend et al., International Patent Publication WO 00/24936, published May 4, 2000) and the most informative members of each cluster are used in subsequent steps. Informative conditions may be picked via the intensity of the observed profile of the experimental condition compared to the profile of a reference condition in a two color assay with the expressed nucleic acids from the reference condition labeled with a first fluorescent dye, and the expressed nucleic acids from the experimental condition labeled with a second, distinguishable fluorescent dye. Alternatively, a single color assay can be performed using the appropriate normalization controls, and the ratios of all possible combinations can be generated using a computer.

5.3. Methods of Using Microarray Cartridges

The cartridges of the present invention may be used in a variety of ways, including, but not limited to, packaging, shipping, storing, and high-throughput processing of microarrays. Examples of methods of using the microarray cartridges of the present invention follow. In many cases, the exemplary methods of use are described in the context of processing nucleic acid microarrays; however one skilled in the art will appreciate that the cartridges of the present invention are suitable for packaging, shipping, storing, and high-throughput processing of any type of microarray, including, but not limited to, those having proteins, ligands, antibodies, adhesion molecules, cellular receptors or other cell fragments or molecules as probes attached to a slide or other suitable substrate.

As stated previously, conventional microarrays are typically placed in microscope slide boxes for shipping and storage, often resulting in damaged or lost microarrays. Thus, an advantage of the cartridges of the present invention is that they can also serve as a shipping container and storage container, with the further advantage that the package is ready for use with automated liquid dispensing robots straight from the manufacturer without costly and time consuming customization. In a preferred method of the present invention, microarrays are placed in cartridges and secured and/or sealed in cartridges during storage. For example, referring to FIGS. 2 and 3, microarray 40 is placed in cartridge 10 as shown and cover 50 is snapped or sealed at one or more edges or points to protect microarray 40 from being damaged by contact or debris during shipping and storage. Cartridge 10 is preferably partially sealed, for example along three edges of the cartridge, using a heat seal or adhesive. The unsealed edge, e.g., the edge having fluted opening 56, 58, is left open to facilitate addition of the processed sample when it is time to use cartridge 10.

Figure 6:
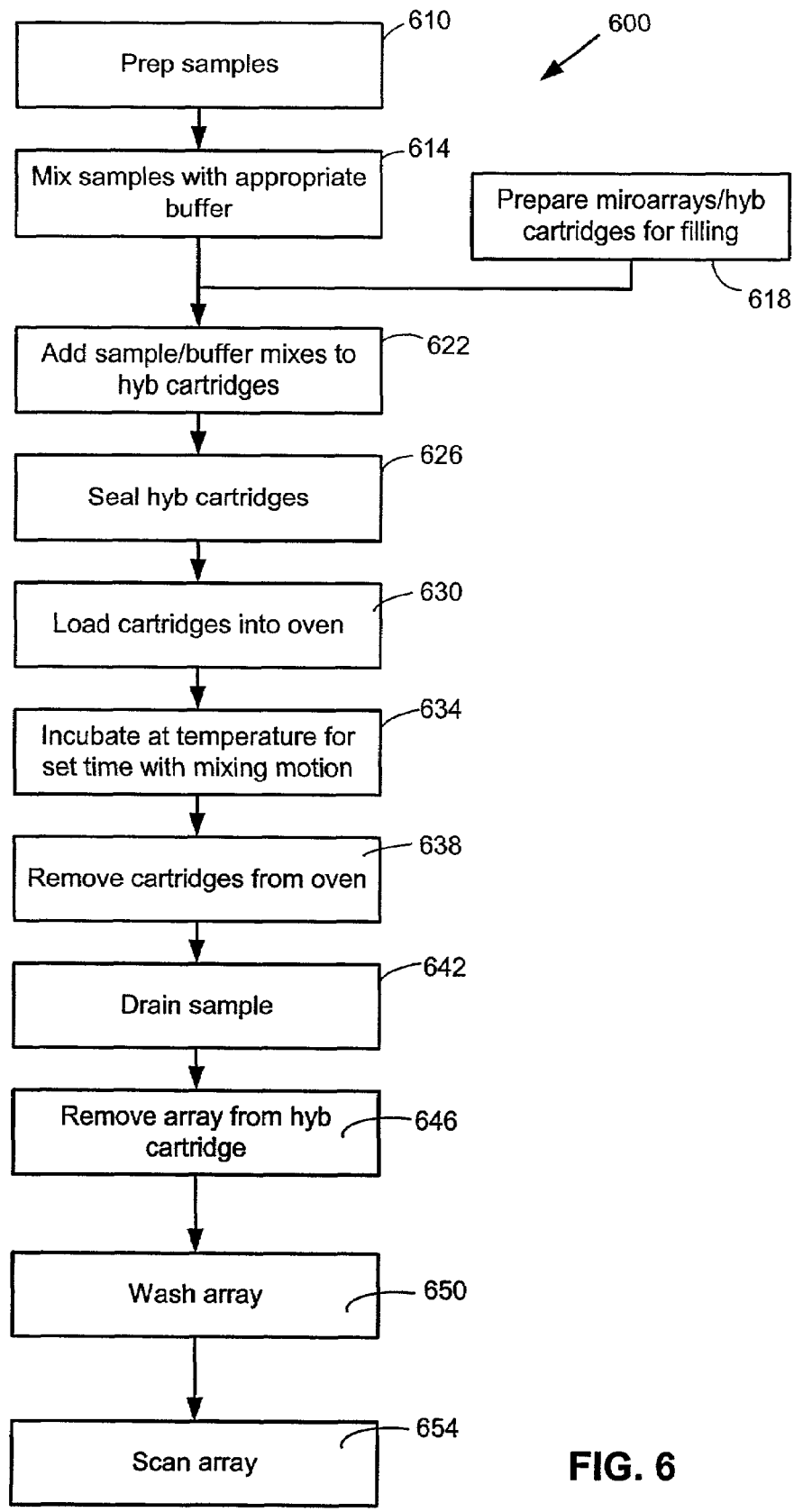
FIG. 6 is a process flow chart of a method for processing microarrays according to the present invention.
Figure 8:
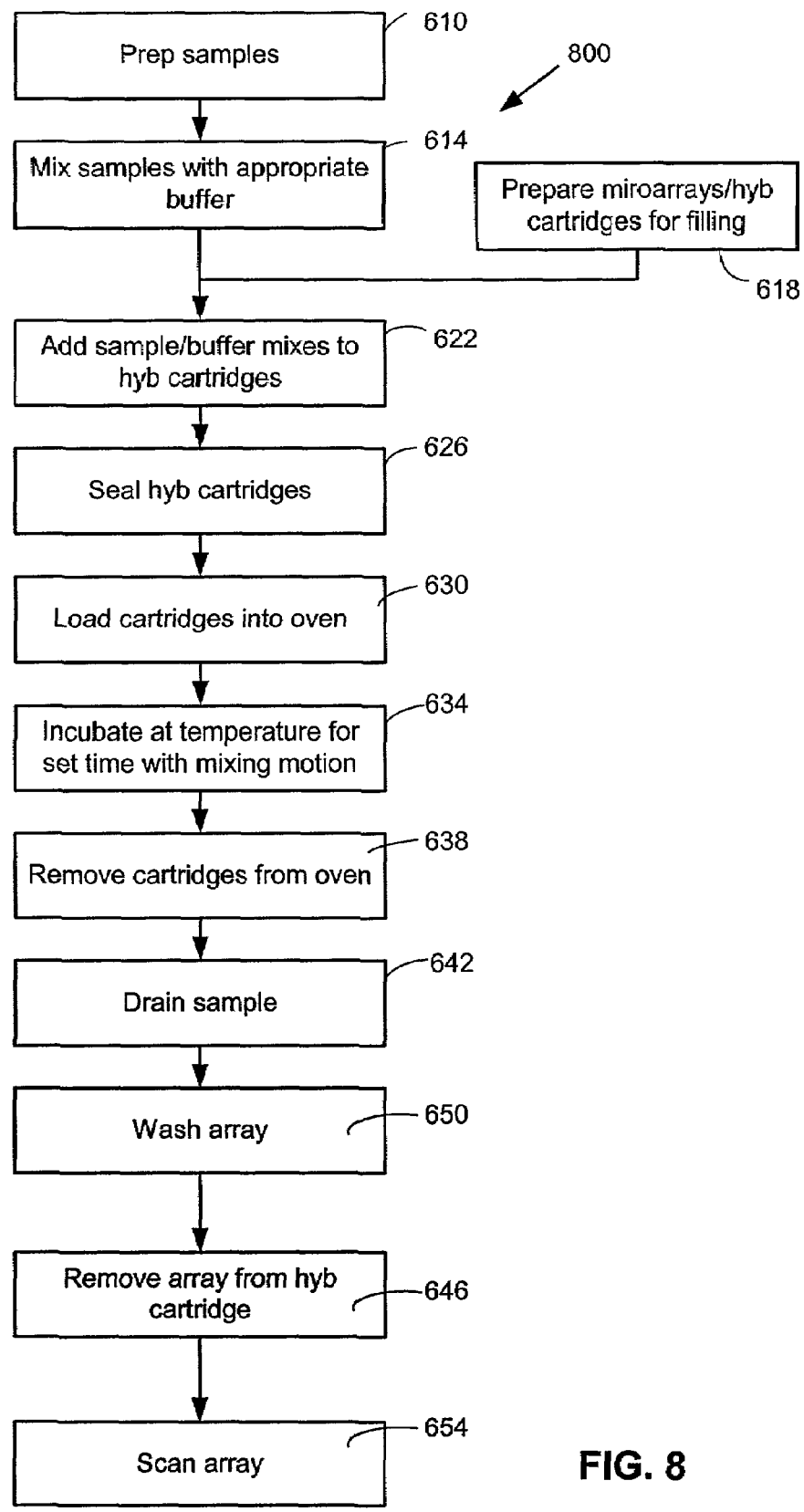
FIG. 8 is a process flow chart of an alternative method for processing microarrays according to the present invention.
Figure 9:
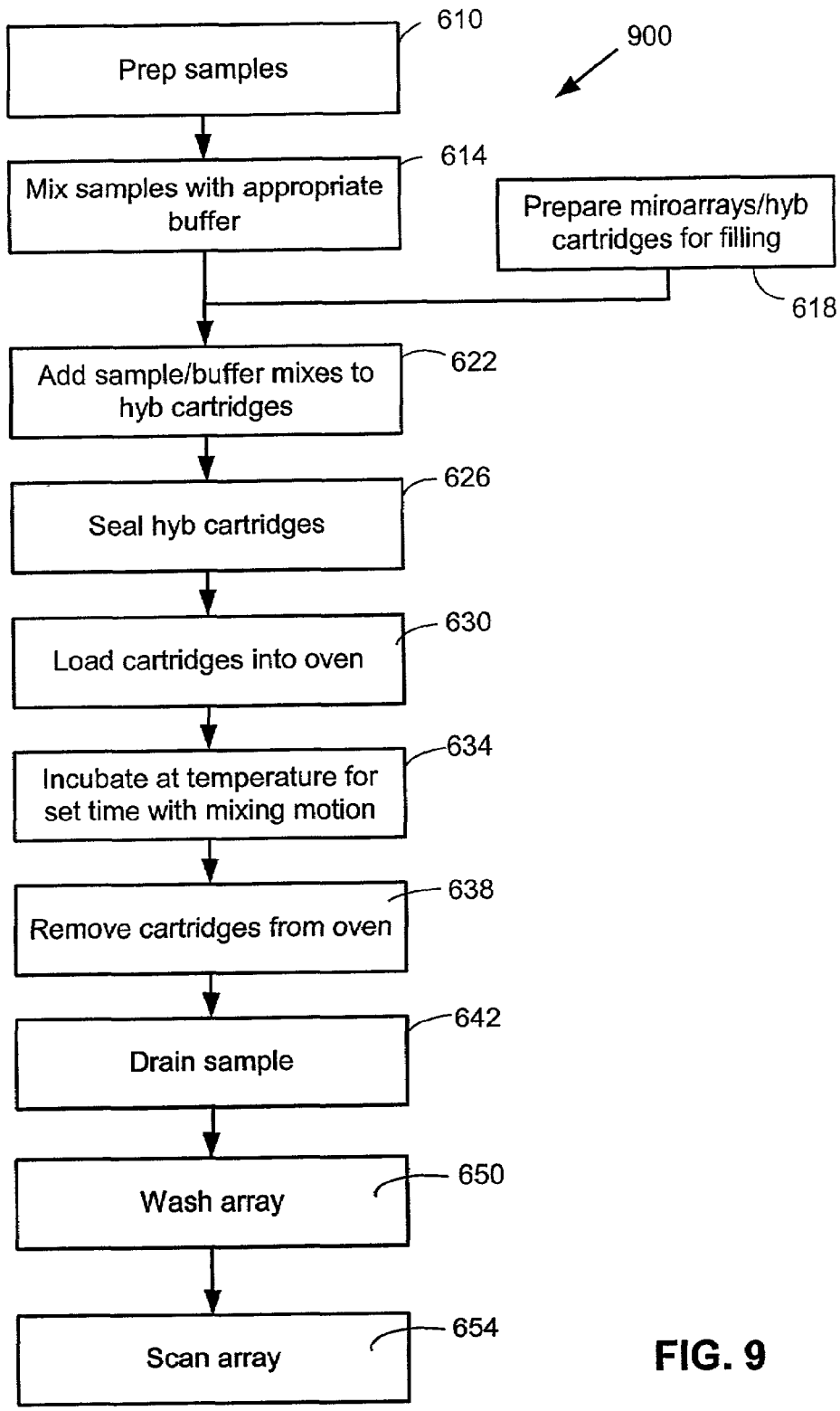
FIG. 9 is a process flow chart of another alternative method for processing microarrays according to the present invention.

Examples of methods of using the cartridges of the present invention are detailed in the process flows 600, 800 and 900 of FIGS. 6, 8 and 9, respectively. The first several steps of processes 600, 800 and 900 are essentially the same. The differences between the alternative processes 600, 800 and 900 relate to whether or not arrays are washed and/or scanned within the microarray cartridges.

Referring to FIG. 6, an initial step in using the microarray cartridges of the present invention, step 610, involves preparing samples of target compounds to be added to the microarrays, for example as discussed above in section 5.2.3. Samples are then mixed with a volume of appropriate buffer in step 614, e.g. 5×SSC plus 0.2% SDS when using cDNA microarrays according to Schena et al., 1996, *Proc. Natl. Acad. Sci. U.S.A.* 93:10614.

In step 618, the microarrays are prepared as described above in section 5.2 above. Nucleic acid microarrays containing double-stranded probe DNA situated thereon (e.g., 'spotter arrays') are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences. Also in step 618, the microarrays are placed in the microarray cartridge (e.g. cartridge 10 of FIGS. 1-4) and fastened or partially sealed as described above.

In step 622, the processed sample solution is added to the microarray in the reaction chamber 30, for example using a robotically controlled pipette or other delivery device inserted through an open edge of cartridge 10 of FIGS. 1-4. Flanges 56, 58 create a fluted opening that helps guide the tip of a delivery device through the un-sealed edge and into a dimple feature 32 or chamber 30 opening. Alternatively, the processed sample may be added by piercing dimple features 32, 34, body 20 or cover 50. In yet another embodiment, the processed sample is added through ports in the body or the cover. Samples are preferably added using a robotic system, such as a Multiprobe II HT robot (Packard Instrument Company, Downer's Grove, Ill.). Alternative equipment that could be used for sample injection includes the Tecan Genesis Workstation (Tecan US Inc, Durham, N.C.), the Biomek FX automatic workstation (Beckman Coulter, Fullerton, Calif.), or custom designed robotic systems. If necessary, the cartridge could be reconfigured to interface with other robotic formats. In addition, manually-operated multi-channel pipetors could be used to introduce reagents into the cartridges in a high-throughput manner. Sample volume is preferably on the order of 50 to 200 µL for a chamber volume of 1 to 3 mL. However other sample sizes and/or chamber volumes may be used without departing from the scope of the invention.

After adding the processed sample, any unsealed edges, ports or holes of the microarray cartridge are sealed in step 626 to prevent leakage of the processed sample solution during incubation. For example, unsealed edges are sealed by heat sealing or adhesive. If samples were added through ports or by piercing the cartridge, any holes are sealed with adhesive, a plug, a heat sealant, etc., preferably by the robotic processing system. For example, the robotic system could be configured with a gasket and/or other sealing device that seals the entry port automatically after the delivery device (e.g., pipette or injection tip) is withdrawn from the cartridge. Alternatively, the ports may consist of resealable elastomeric septums through which the sample solution is injected.

Figure 7:
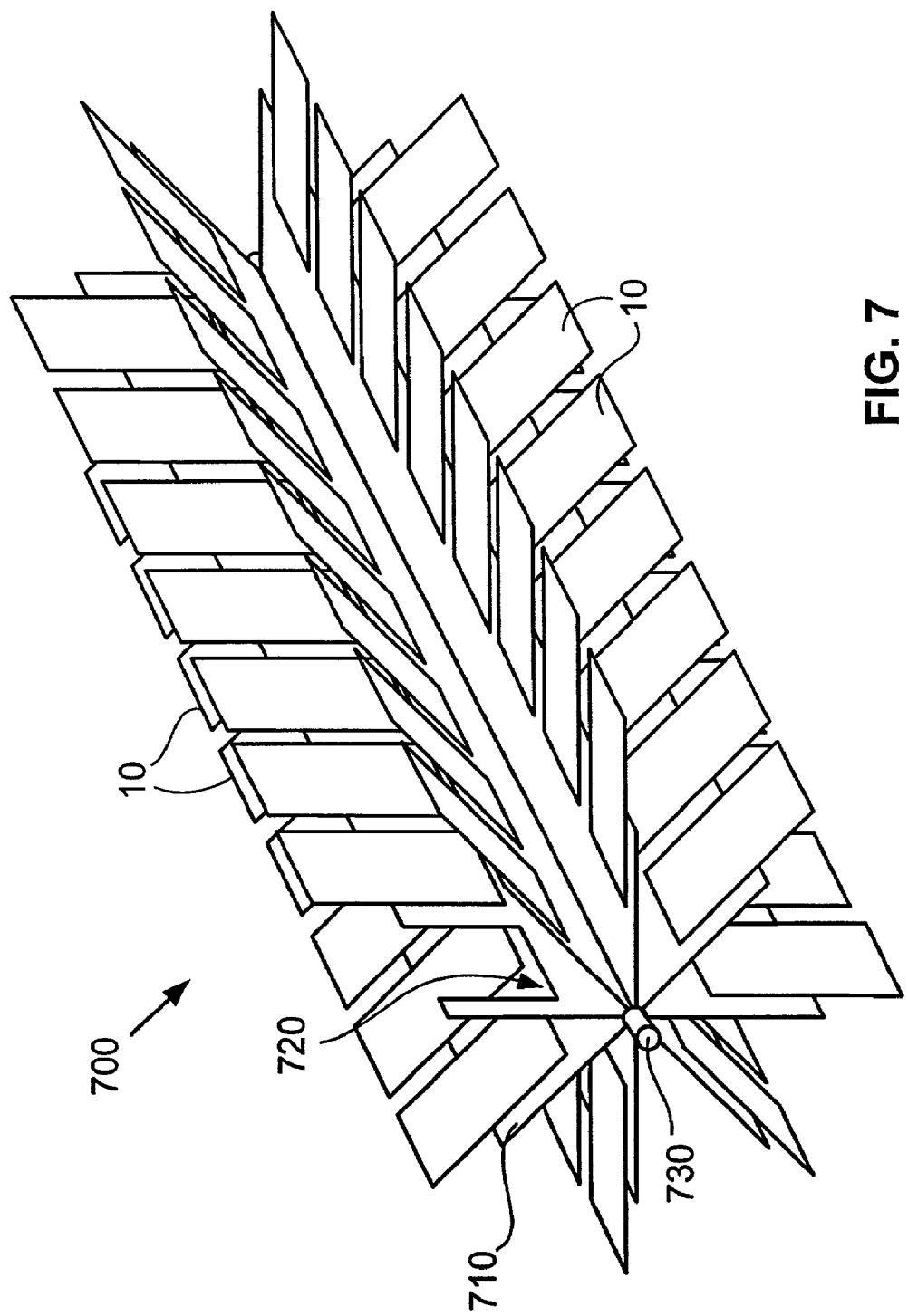
FIG. 7 is a perspective view of a wheel for holding and rotating a plurality of microarray cartridges according to the present invention.

After adding processed sample solution to the microarray and sealing the cartridge, one or more cartridges are placed in an oven in step 630. Preferably, a number of cartridges are placed in a mixing device, such as a rotating wheel or a rocker platform, and the entire device is placed inside an oven. For example, FIG. 7 shows a wheel 700 suitable for holding and rotating a large number, e.g. 128, of cartridges at a time. Wheel 700 includes a number of fins, or vanes 710, each configured to hold a number of cartridges 10. For example, wheel 700 includes eight vanes 710, each vane includes eight slots 720, and each slot is configured to hold at least one cartridge 10. In use, the cartridges 10 are loaded onto wheel 700 and the entire wheel is placed in a holder (not shown) in the oven. One skilled in the art will appreciate that wheel 700 may include any number of vanes, each holding any number of cartridges, depending upon the desired application. For example, one embodiment includes sixteen vanes, each configured to hold four cartridges.

Step 634 entails incubating the arrays within the cartridges inside the oven at a particular temperature while mixing and flowing the processed sample over the array. For example, wheel 700 is rotated about its central axis 730 at a set rate, e.g. 20 rpm, to provide continuous mixing and flow of the processed samples over the arrays. Frequency of rotation or rocking may be modified to optimize reaction conditions, and obstacles (e.g. obstacles 560 of FIG. 5) may be used in the reaction chamber to facilitate mixing as describe above.

Reactions are typically performed in the range of 40° C. to 65° C., depending upon the nature of the microarray probes. An exemplary embodiment uses 60mer oligonucleotides probes selected using the oligo design principles articulated in Hughes et aL, 2001, *Nat. Bio.* 19:342-347. Using such 60 mer microarrays, for example, the hybridization reaction is performed at 40° C. for 24 hours.

In order to achieve high quality reaction data, it is advantageous to incubate microarray reactions in a fashion that causes the biological sample solution to be continuously mixed as it flows over the microarray probe surface as describe above. Reaction chamber volume in the cartridges of the present invention are dimensioned to provide optimal flow and mixing for a given sample solution volume using the principles taught herein. In addition, quality and uniformity of reactions over the entire microarray probe matrix may be improved by constructing the cartridge of material that flexes as the sample solution washes from side to side in the chamber as the cartridge is rotated or rocked in the oven. Minimizing the volume of solution that gets trapped behind the array also tends to lead to better reactions. Thus, the supports (e.g. ledges 26, 28 of FIGS. 1-4) that position a microarray within a cartridge and define the reaction chamber are preferably dimensioned to minimize space behind the microarray.

To achieve higher microarray throughput, the present invention contemplates stacking cartridge packs on a fixture, such as a rocker platform or a rotating wheel, and either rocking or rotating the whole fixture in an oven. In this manner, at least 64 to 128 samples may be analyzed in a single oven, as compared with a maximum of 96 per oven using a conventional hybridization bag method. Alternative approaches include custom heat strips or trays with temperature controls, dipping cartridges into temperature-controlled water baths, or setting the cartridges in a temperature-controlled air stream.

After incubating the arrays in step 634, the cartridges are removed from the oven in step 638. The sample is then drained from each cartridge in step 642 and each array is removed from its reaction chamber in step 646. Draining the sample may be performed by piercing the reaction chamber, e.g. at a dimple feature, or by simple cutting off an edge of the chamber to expose the array.

In step 650, microarrays are washed with buffers as a final processing step prior to scanning in step 654. Washing removes background signal and provides a final level of stringency for quality data. In process 600, washing takes place with microarrays removed from cartridges, e.g. by washing buffers over the microarrays (either by bath dipping or in flow streams). Because the microarrays of the present invention preferably have hydrophobic surfaces outside the array dots, water does not adhere well to the surface, a drying step is not typically needed. However, if desired, an air knife or flow could be developed to dry the microarrays in batch. For example, the arrays may be dried using nitrogen or a centrifuge to spin-dry. There is also the potential to scan the microarrays in the cartridge without washing, if a confocal microscope can reduce background sufficiently. In step 654 the processed microarrays are placed into a suitable microarray scanning instrument and scanned as mentioned above and as detailed in U.S. Pat. No. 6,225, 645.

Referring to FIG. 8, an alternative method 800 of processing microarrays is essentially the same as method 600, except that washing the array (step 650) is performed before removing the array from the reaction chamber (step 646). An advantage leveraged by this invention is the ability to wash microarrays in batches. Batch processing is more compatible for generating data within an experimental run, especially when comparing sample-control pairs. Alternatively, washing within the reaction chamber could be implemented, for example, by flowing wash buffer through the microarray cartridge dimple features and over the microarrays using, for example, the Packard Multiprobe II to inject wash buffer. Alternatively, a custom designed robotic device could be used to wash the array, including an agitation step and a final nitrogen flow to dry the microarray. One skilled in the art will recognize that there are a variety of other methods to implement washing within the microarray cartridge, including making injections, incisions or dye cuts into the cartridge and flowing wash buffer over the array or placing the entire cartridge in a flow stream or bath.

Referring to FIG. 9, an alternative method 900 of processing microarrays is essentially the same as methods 600 and 800, except that the step of removing the array form the reaction chamber (step 646) is omitted from process 900. Thus, in method 900, the arrays are scanned while in the reaction chamber. Optical properties or other features of the reaction chamber may be modified by one skilled in the art to optimize scanning of the microarray through the body of the chamber.

In general, nucleic acid hybridization and wash conditions are chosen so that the polynucleotide molecules to be analyzed by the invention "specifically bind" or "specifically hybridize" to the complementary polynucleotide sequences of the array, preferably to a specific array site, wherein its complementary DNA is located.

Optimal hybridization conditions will depend on the length (e.g., oligomer versus polynucleotide greater than 200 bases) and type (e.g., RNA or DNA) of probe and target nucleic acids. General parameters for specific (i.e., stringent) hybridization conditions are described in Sambrook et al. (supra), and in Ausubel et al., 1987, Current Protocols in Molecular Biology, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in high stringency wash buffer (0.1×SSC plus 0.2% SDS) (Shena et al., 1996, Proc. Natl. Acad. Sci. U.S.A. 93:10614). Useful hybridization conditions are also provided, e.g., Tijessen, 1993, Hybridization With Nucleic Acid Probes, Elsevier Science Publishers B.V.; and Kricka, 1992, Nonisotopic DNA Probe Techniques, Academic Press, San Diego, Calif.

While the exemplary methods of the invention are described in the context of hybridizing nucleic acid microarray probes with nucleic acid samples, one skilled in the art will appreciate that the apparatus and methods described herein encompass the use of other probe-sample combinations, including but not limited to, protein-protein, protein-ligand, enzyme-substrate, antibody-antigen, and other combinations.

6. REFERENCES CITED

All references cited herein are incorporated herein by reference in their entirety and for all purposes to the same extent as if each individual publication or patent or patent application was specifically and individually indicated to be incorporated by reference in its entirety for all purposes.

While the invention is susceptible to various modifications and alternative forms, specific examples thereof have been shown in the drawings and are herein described in detail. It should be understood, however, that the invention is not to be limited to the particular forms or methods disclosed, but rather the invention is to cover all modifications, equivalents and alternatives falling within the spirit and scope of the appended claims.

What is claimed is:

1. A microarray cartridge, comprising:
   a body having a wall forming a cavity surrounded by a mating surface, said body comprising a reaction chamber and at least one microarray support contained within the cavity, said at least one microarray support supporting a microarray slide within the cavity such that a surface of the slide covers the reaction chamber; and
   a cover that (a) is covering the cavity such that said slide is disposed between said cover and the reaction chamber, and (b) is sealingly adhered with the mating surface of said body by non-removable adhering means on all but one edge of the mating surface, said all but one edge being unsealed to said cover.

2. The microarray cartridge of claim 1, wherein the non-removable adhering means comprises a heat seal between said cover and the mating surface of said body.

3. The microarray cartridge of claim 1, wherein the non-removable adhering means comprises a non-removable adhesive seal between said cover and the mating surface of said body.

4. The microarray cartridge of claim 1, wherein the non-removable adhering means does not include a mechanical fastener.

5. The microarray cartridge of claim 1, further comprising a plurality of microarray supports within the cavity for positioning the microarray slide.

6. The microarray cartridge of claim 1, wherein the cartridge further comprises a first access site communicating with the reaction chamber for passing fluids from a delivery device and into the reaction chamber.

7. The microarray cartridge of claim 6, wherein the first access site is located on said body, wherein the access site is dimensioned to pass fluids from a fluid delivery device through the body wall and into the reaction chamber.

8. The microarray cartridge of claim 6, wherein the body further comprises a first dimple feature in communication with the reaction chamber and the first access site, the first dimple feature forming a passage within the body for a fluid around a first edge of the microarray slide and into the reaction chamber when the microarray slide is placed in the cavity.

9. The microarray cartridge of claim 8, wherein the first access site is located on said body and communicates with said dimple feature, such that fluid from the fluid delivery device passes through the body wall and into the dimple feature.

10. The microarray cartridge of claim 8, wherein the first access site is located on said cover and communicates with said dimple feature, such that fluid from the fluid delivery device passes through the cover and into the dimple feature.

11. The microarray cartridge of claim 10, wherein the first access site is an open port and the fluid delivery device is a pipette dimensioned to deliver fluids through the port.

12. The microarray cartridge of claim 10, wherein the first access site has a thickness of between 0.003 and 0.015 inches, and the fluid delivery device is a needle for piercing through the access site and delivering fluids into the first dimple feature.

13. The microarray cartridge of claim 8, wherein said body further comprises a second dimple feature in communication with the reaction chamber, the second dimple feature forming a passage for fluids around a second edge of the microarray slide and into the reaction chamber when the microarray slide is placed in the cavity.

14. The microarray cartridge of claim 13, wherein said cartridge further includes a second access site communicating with the second dimple feature for passing fluids into or out of the reaction chamber.

15. The microarray cartridge of claim 6, wherein the first access site is an open end of the cartridge at said unsealed edge, said cartridge further comprising a flange feature at the open end to facilitate entry of a fluid delivery device through the first access site before sealingly cohering said cover to said body at the open end.

16. The microarray cartridge of claim 15, wherein the flange feature comprises a first flange attached to and extending from an edge of said body at the access site and a second flange attached to and extending from a corresponding edge of said cover, such that the first and second flanges facilitate passage of the fluid delivery device through the open end of the cartridge between the body and the cover.

17. The microarray cartridge of claim 1, wherein the body is thermoformed and the body wall has a thickness of less than 0.065 inch.

18. The microarray cartridge of claim 17, wherein the thickness is between 0.005 and 0.025 inch.

19. The microarray cartridge of claim 18, wherein the thickness is between 0.010 and 0.015 inch.

20. The microarray cartridge of claim 1, wherein the body is injection molded and the body wall has a thickness of less than 0.1 inch.

21. The microarray cartridge of claim 20, wherein the thickness is between 0.032 and 0.075 inch.

22. The microarray cartridge of claim 21, wherein the thickness is between 0.040 and 0.060 inches.

23. The microarray cartridge of claim 1, wherein the body includes a plurality of cavities, each of the plurality of cavities having a corresponding reaction chamber and at least one corresponding microarray support for supporting a microarray slide.

24. The microarray cartridge of claim 23, wherein the plurality of cavities comprises at least four cavities.

25. The microarray cartridge of claim 1, wherein reaction chamber has a volume of at least 500 μL.

26. The microarray cartridge of claim 25, wherein the volume is at least 1 mL.

27. The microarray cartridge of claim 26, wherein the volume is 1 mL to 3 mL.

28. The microarray cartridge of claim 1, wherein the body further comprises a plurality of obstacles within the reaction chamber arranged to affect motion of fluid within the chamber.

29. The microarray cartridge of claim 28, wherein the obstacles are attached to a surface of the reaction chamber opposite the microarray slide.

30. The microarray cartridge of claim 1 wherein the microarray slide comprises an array of nucleic acid probes distributed on the surface of a glass substrate, and wherein the microarray slide is positioned such that the probes are in communication with a fluid in the reaction chamber.

31. The microarray cartridge of claim 30, wherein the fluid includes nucleic acid molecules under conditions conducive to hybridization between the nucleic acid molecules and the nucleic acid probes on the microarray.

32. The microarray cartridge of claim 1, wherein said cover contiguously extends from an edge of the mating surface and hingably covers the cavity and sealingly adheres with the mating surface of said body.

* * * * *